United States Patent
Dumoulin-White et al.

(12) 
(10) Patent No.: US 11,793,818 B2
(45) Date of Patent: Oct. 24, 2023

(54) METHOD FOR TREATING CONDITIONS ASSOCIATED WITH HYPERPROLIFERATING CELLS COMPRISING COMBINED ADMINISTRATION OF A CANNABINOID RECEPTOR AGONIST AND RADIATION THERAPY

(71) Applicant: Theralase Technologies, Inc., Toronto (CA)

(72) Inventors: Roger Dumoulin-White, Toronto (CA); Arkady Mandel, North York (CA)

(73) Assignee: THERALASE TECHNOLOGIES, INC., Toronto (CA)

( * ) Notice: Subject to any disclaimer, the term of this patent is extended or adjusted under 35 U.S.C. 154(b) by 0 days.

(21) Appl. No.: 16/365,148

(22) Filed: Mar. 26, 2019

(65) Prior Publication Data

US 2019/0290657 A1   Sep. 26, 2019

Related U.S. Application Data

(60) Provisional application No. 62/648,334, filed on Mar. 26, 2018.

(51) Int. Cl.
| | |
|---|---|
| A61K 31/555 | (2006.01) |
| A61K 41/00 | (2020.01) |
| A61K 47/64 | (2017.01) |
| A61K 31/352 | (2006.01) |

(52) U.S. Cl.
CPC .......... *A61K 31/555* (2013.01); *A61K 31/352* (2013.01); *A61K 41/0057* (2013.01); *A61K 47/644* (2017.08)

(58) Field of Classification Search
CPC ............... A61K 31/352; A61K 31/555; A61K 41/0057; A61K 47/644
See application file for complete search history.

(56) References Cited

U.S. PATENT DOCUMENTS

| | | | |
|---|---|---|---|
| 6,962,910 B2 | 11/2005 | Brewer et al. | |
| 7,612,057 B2 | 11/2009 | Brewer et al. | |
| 8,148,360 B2 | 4/2012 | Brewer et al. | |
| 8,445,475 B2 | 5/2013 | Brewer et al. | |
| 9,345,769 B2 | 5/2016 | Mcfarland | |
| 9,737,565 B2 * | 8/2017 | Mandel | A61K 9/0009 |
| 10,111,936 B2 * | 10/2018 | Mandel | A61K 38/40 |
| 10,335,608 B2 * | 7/2019 | Mandel | A61K 31/4745 |
| 10,525,279 B2 * | 1/2020 | Mandel | A61P 35/00 |
| 2016/0039854 A1 | 2/2016 | Mcfarland | |
| 2016/0206653 A1 * | 7/2016 | Mandel | A61K 38/40 |
| 2016/0271100 A1 * | 9/2016 | Sawyer | A61K 31/495 |

FOREIGN PATENT DOCUMENTS

WO   WO-2016057840 A1 *   4/2016   ............ A61K 36/47

OTHER PUBLICATIONS

Scott et al. Mol. Cancer Ther., 13(12), Dec. 2014, pp. 2955-2967. (Year: 2014).*
Chakravarti et al. (2014). Cannabinoids as therapeutic agents in cancer: current status and future implications, Oncotarget, 5(15), 5852-5872.

* cited by examiner

*Primary Examiner* — Kara R McMillian
(74) *Attorney, Agent, or Firm* — CAESAR RIVISE, PC

(57) ABSTRACT

Disclosed is a method for treating a condition associated with hyperproliferating cells, the method including the steps of administering to a subject having the condition a composition including at least one cannabinoid receptor agonist, optionally administering to the subject a photodynamic compound, and administering radiation to the subject in whom the at least one cannabinoid receptor agonist is present so as to treat the condition.

20 Claims, 1 Drawing Sheet

METHOD FOR TREATING CONDITIONS ASSOCIATED WITH HYPERPROLIFERATING CELLS COMPRISING COMBINED ADMINISTRATION OF A CANNABINOID RECEPTOR AGONIST AND RADIATION THERAPY

BACKGROUND OF THE INVENTION

1. Field of Invention

This invention relates to methods for treating conditions associated with hyperproliferating cells and more particularly to such methods comprising the use of radiation therapy.

2. Description of Related Art

Photodynamic therapy ("PDT") is currently an active area of research for the treatment of diseases associated with hyperproliferating cells such as cancer and non-malignant lesions. The development of new photodynamic compounds ("PDCs") or photosensitizers ("PSs") for PDT has been increasingly focused on metallosupramolecular complexes derived from metals. For example, WO 2013158550 A1 and WO 2014145428 A2 disclose metal based PDCs useful as in vivo diagnostic agents, as therapeutic agents for treating or preventing diseases that involve unwanted and/or hyperproliferating cell etiology, including cancer, as agents for treating infectious diseases, and as agents for pathogen disinfection and/or sterilization. U.S. Pat. Nos. 6,962,910, 7,612,057, 8,445,475 and 8,148,360 disclose supramolecular metal complexes capable of cleaving DNA when irradiated by low energy visible light with or without molecular oxygen.

Another active area of research for the treatment of diseases associated with hyperproliferating cells relates to the use of cannabinoids for treating cancer. See, e.g., Chakravarti et al. "Cannabinoids as therapeutic agents in cancer: current status and future implications." Oncotarget 5.15 (2014): 5852.

Despite the foregoing developments, it is desired to provide additional compounds, compositions and therapeutic methods for treating conditions associated with hyperproliferating cells.

All references cited herein are incorporated herein by reference in their entireties.

BRIEF SUMMARY OF THE INVENTION

Accordingly, one aspect of the invention comprises a method for treating a condition associated with hyperproliferating cells, said method comprising the steps of: (a) administering to a subject having the condition a composition comprising at least one cannabinoid receptor agonist; (b) optionally administering to the subject a photodynamic compound; and (c) administering radiation to the subject in whom the at least one cannabinoid receptor agonist is present so as to treat the condition.

In certain embodiments, the at least one cannabinoid receptor agonist is delta9-tetrahydrocannabinol or cannabidiol.

In certain embodiments, the radiation is infrared light, visible light, X-rays or other ionizing radiation.

In certain embodiments, the condition is cancer.

In certain embodiments, the composition and the radiation are administered in amounts synergistically effective to treat the condition.

In certain embodiments, the composition is administered so as to administer to the subject the at least one cannabinoid receptor agonist in an amount of at least 40 μM.

In certain embodiments, the photodynamic compound is administered to the subject before step (a) is conducted.

In certain embodiments, the photodynamic compound is administered in combination with a metal binding glycoprotein.

In certain embodiments, the photodynamic compound is represented by the following structure:

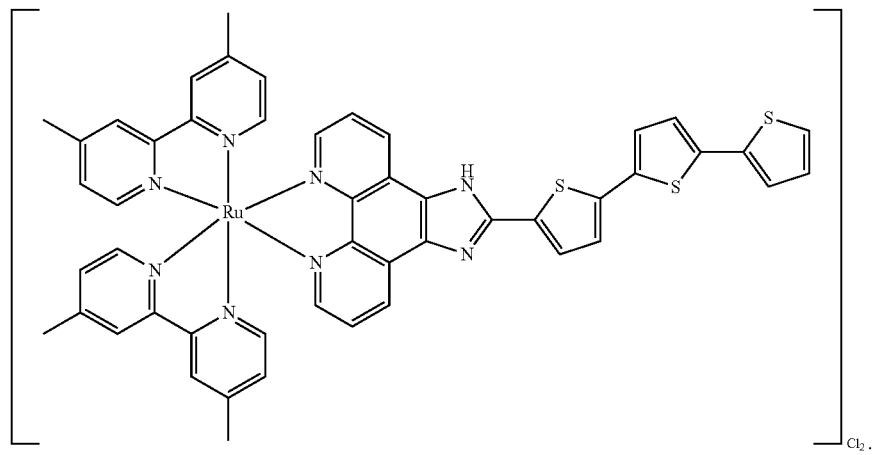

In certain embodiments, the metal binding glycoprotein is transferrin.

In certain embodiments, the at least one cannabinoid receptor agonist, the photodynamic compound and the radiation are administered in amounts synergistically effective to treat the condition.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF PREFERRED EMBODIMENTS OF THE INVENTION

Figure 1:
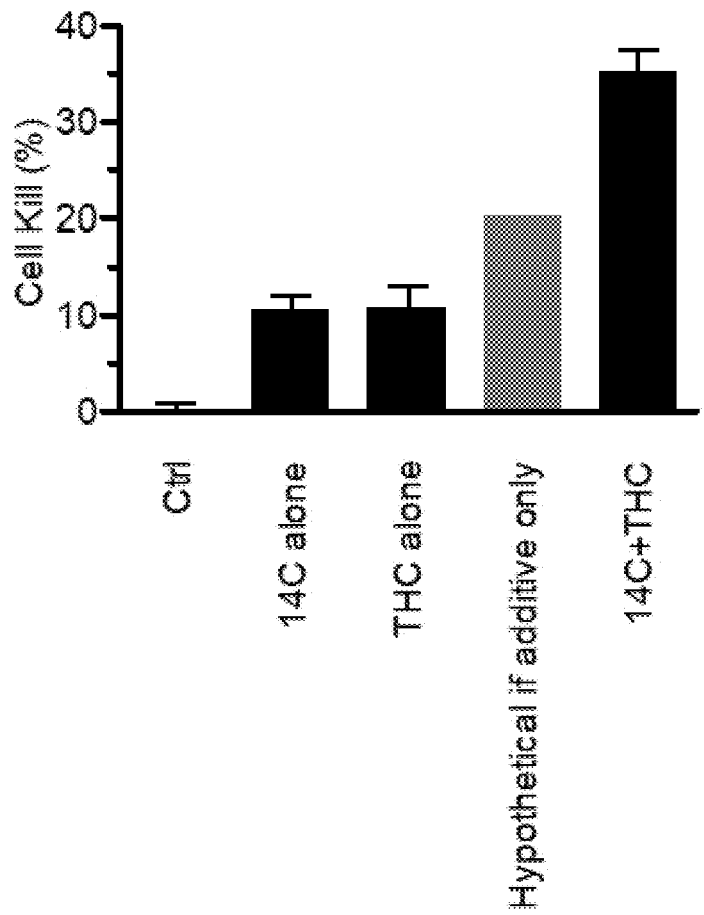
FIG. 1 is a bar graph of cell kill percentages.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously Cannabinoid Receptor Agonists and PDCs Compositions of the invention comprise at least one cannabinoid receptor agonist. Preferred cannabinoid receptor agonists can be natural or synthetic CB1 and/or CB2 receptor agonists, including cannabinoids (and salts thereof). More preferably, the cannabinoid receptor agonist is delta9-tetrahydrocannabinol or cannabidiol. The compositions preferably further comprise a pharmaceutically acceptable excipient.

PDCs suitable for use in the invention include, but are not limited to those disclosed in WO 2013158550 A1, WO 2014145428 A2, U.S. Pat. Nos. 6,962,910, 7,612,057, 8,445,475 and 8,148,360.

The PDC when used in the inventive method is preferably administered in a composition further comprising a pharmaceutically acceptable excipient. The composition can still further comprise the cannabinoid receptor agonist or it can be a composition separate from that of the cannabinoid receptor agonist.

For the purposes of the present invention the terms "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery, but also as a means for achieving effective absorption by the recipient of the active ingredient. An excipient may fill a role as simple and direct as being an inert filler, or an excipient as used herein may, for example, be part of a pH stabilizing system or coating to insure delivery of the ingredients safely to the stomach. The formulator can also take advantage of the fact that the active agents of the present invention have improved cellular potency, improved pharmacokinetic properties, as well as improved oral bioavailability.

The present teachings also provide pharmaceutical active agents that include at least one compound described herein and one or more pharmaceutically acceptable carriers, excipients or diluents. Examples of such carriers are well known to those skilled in the art and can be prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Cannabinoid receptor agonists and PDCs (hereinafter sometimes referred to collectively and separately as "active agent(s)") of the invention can be administered orally, intravenously, intravesically, intratumourally, topically or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents or encapsulating materials. The active agents can be formulated in conventional manner, for example, in a manner similar to that used for known active agents. Oral formulations containing an active agent disclosed herein can comprise any conventionally used oral form, including tablets, capsules, buccal forms, troches, lozenges and oral liquids, suspensions or solutions. In powders, the carrier can be a finely divided solid, which is an admixture with a finely divided active agent. In tablets, an active agent disclosed herein can be mixed with a carrier having the necessary compression properties in suitable proportions and compacted in the shape and size desired. The powders and tablets can contain up to 99% of the active agent.

Capsules can contain mixtures of one or more compound(s) and/or compositions disclosed herein with inert filler(s) and/or diluent(s) such as pharmaceutically acceptable starches (i.e., corn, potato or tapioca starch), sugars, artificial sweetening agents, powdered celluloses (i.e., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine Oral formulations herein can utilize standard delay or time-release formulations to alter the absorption of the compound(s) and/or compositions. The oral formulation can also consist of administering an active agent disclosed herein in water or fruit juice, containing appropriate solubilizers or emulsifiers as needed.

Liquid carriers can be used in preparing solutions, suspensions, emulsions, syrups, elixirs and for inhaled delivery. An active agent of the invention can be dissolved or suspended in a pharmaceutically acceptable liquid carrier such as water, an organic solvent, or a mixture of both, or a pharmaceutically acceptable oil or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, i.e., cellulose derivatives such as a sodium carboxymethyl cellulose solution), alcohols (including monohydric alcohols and polyhydric alcohols, i.e., glycols) and their derivatives, and oils (i.e., fractionated coconut oil and *arachis* oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal, topical or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules or suppositories. In such form, the pharmaceutical composition can be subdivided in unit dose(s) containing appropriate quantities of the active agent. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of each active agent to about 500 mg/kg of each active agent and can be given in a single dose or in two or more doses. Such doses can be administered in any manner useful in directing the compound(s) and/or composition(s) to the recipient's bloodstream, including orally, via implants, parenterally (including intravenous, intraperitoneal, topical and subcutaneous injections), rectally, vaginally, and transdermally.

When administered for the treatment or inhibition of a particular disease state or disorder, it is understood that an effective dosage can vary depending upon the particular active agent utilized, the mode of administration and severity of the condition being treated, as well as the various physical factors related to the individual being treated. In therapeutic applications, an active agent can be provided to a patient already suffering from a disease in an amount sufficient to heal or at least partially ameliorate the symptoms of the disease and its complications. The dosage to be used in the treatment of a specific individual typically must be subjectively determined by the attending physician. The variables involved include the specific condition and its state as well as the physical size, age, gender, health status and response pattern of the patient.

In some cases, it may be desirable to administer an active agent directly to the airways of the patient, using devices such as, but not limited to, metered dose inhalers, breath-operated inhalers, multidose dry-powder inhalers, pumps, squeeze-actuated nebulized spray dispensers, aerosol dispensers and aerosol nebulizers. For administration by intranasal or intrabronchial inhalation, the active agent(s) can be formulated into a liquid composition, a solid composition, or an aerosol composition. The liquid composition can include, by way of illustration, one or more active agents dissolved, partially dissolved or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more active agents intermixed with lactose or other inert powders that are acceptable for intrabronchial use, and can be administered by, for example, an aerosol dispenser or a device that breaks or punctures a capsule encasing the solid active agent and delivers the solid active agent for inhalation. The aerosol active agent can include, by way of illustration, one or more active agents, propellants, surfactants, and co-solvents, and can be administered by, for example, a metered device. The propellants can be a ChloroFluoroCarbon ("CFC"), a HydroFluoroAlkane ("HFA"), or other propellants that are physiologically and environmentally acceptable.

Active agents of the invention can be administered parenterally or intraperitoneally. Solutions or suspensions of these active agents or pharmaceutically acceptable salts, hydrates, or esters thereof can be prepared in water suitably mixed with a surfactant such as hydroxyl-propylcellulose. Dispersions can also be prepared in propylene glycol, glycerol, liquid polyethylene glycols and/or mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In certain embodiments, the form can be sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (i.e., propylene glycol, glycerol and liquid polyethylene glycol), and/or suitable mixtures thereof in oils.

Active agents described herein can be administered transdermally, (i.e., administered across the surface of the body and the inner linings of bodily passages including epithelial and mucosal tissues). Such administration can be carried out using the active agents of the invention including pharmaceutically acceptable salts, hydrates, or esters thereof, in lotions, creams, foams, patches, suspensions, solutions and/or suppositories (rectal and vaginal).

Transdermal administration can be accomplished through the use of a transdermal patch containing an active agent disclosed herein, and a carrier that can be inert to the active agent, can be non-toxic to the skin, and can allow delivery of the active agent for systemic absorption into the blood stream via the skin. The carrier can take any number of forms such as creams and ointments, pastes, gels and occlusive devices. The creams and ointments can be viscous liquid or semisolid emulsions of either the oil-in-water or water-in-oil type. Pastes comprised of absorptive powders dispersed in petroleum or hydrophilic petroleum containing the active agent can also be suitable. A variety of occlusive devices can be used to release the active agent into the blood stream, such as a semi-permeable membrane covering a reservoir containing the active agent with or without a carrier, or a matrix containing the active agent. Other occlusive devices are known in the literature.

Compounds and/or composition described herein can be administered rectally or vaginally in the form of a conventional suppository. Suppository formulations can be made from traditional materials, including cocoa butter, with or without the addition of waxes to alter the suppository's melting point and/or glycerin. Water-soluble suppository bases, such as polyethylene glycols of various molecular weights, can also be used.

Lipid formulations or nanocapsules can be used to introduce active agents into host cells either in vitro or in vivo. Lipid formulations and nanocapsules can be prepared by methods known in the art.

To increase the effectiveness of active agents, it can be desirable to combine an active agent with other agents effective in the treatment of the target disease. For example, other active agents effective in treating the target disease can be administered with the active agents. The other agents can be administered at the same time or at different times than the active agents disclosed herein.

Active agents of the invention can be useful for the treatment or inhibition of a pathological condition or disorder in a mammal, for example, a human subject. The invention accordingly provides methods of treating or inhibiting a pathological condition or disorder by providing to a mammal an active agent of the invention.

Non-limiting examples of the active agent comprise the active agent in amounts from about 0.001 mg to about 1000 mg or 0.01 mg to 100 mg or 0.1 mg to 10 mg.

Therapeutic Method

The method of the invention comprises administering to a subject (i.e., an animal, and preferably a mammal, such as a human) an effective amount of at least one cannabinoid receptor agonist and administering radiation to the subject in whom the at least one cannabinoid receptor agonist is present so as to treat the condition. The method optionally includes the additional step of administering to the subject a PDC.

Suitable methods for administering the active agent(s) are discussed above.

The active agent is preferably administered in an amount of at least 40 μM before radiation is administered and preferably before administering the PDC, if any.

Radiation is administered to the subject to activate the cannabinoid and/or any PDCs present and/or to provide a synergistically effective combination with the cannabinoid receptor agonist(s) to treat the condition. The term "radiation" as used herein encompasses non-ionizing radiation and ionizing radiation of the electromagnetic spectrum, including infrared light, visible light, X-rays, Y-rays and quanta, and corpuscular radiation (a-particles, p-particles, positrons, neutrons and heavy particles) capable of producing ions. Suitable wavelengths of radiation applied include, but are not limited to 180 to 1000 nm and most preferably 400 to 950 nm.

Radiation is directly ionizing if it carries an electric charge that directly interacts with atoms in the tissue or medium by electrostatic attraction. Indirect ionizing radiation is not electrically charged, but results in production of charged particles by which its energy is absorbed. It takes about 34 eV of energy to produce an ionization. Most human exposures to radiation are of energies of 0.05-5 million electron volts (MeV)—energies at which many ionizations occur as the radiation passes through cells. Most X-rays have a wavelength ranging from 0.001 to 10 nanometers. In the case of using a radioenhancer, a patient can be treated with a "diagnostic" dose of ionizing radiation, such as 0.02 Gy.

The radiation can be applied systemically or locally, topically or internally. The radiation is administered in a safe and effective dosage. For example, laser light is preferably administered in a dosage of at least 10 $J/cm^2$, preferably 10 or 100 $J/cm^2$ and more preferably from 25 to 90 $J/cm^2$. Radiation is preferably administered at a predetermined fluence rate or radiation dose to achieve the most desirable therapeutic effect—up to the highest permissible radiation dose, based on the patient's clinical status.

The method is synergistically effective for treating conditions associated with hyperproliferating cells, such as benign and malignant tumors.

The invention will be illustrated in more detail with reference to the following examples, but it should be understood that the present invention is not deemed to be limited thereto.

EXAMPLES

Example 1

Glioma cells were treated with delta9-tetrahydrocannabinol ("d9-THC") for 24 hours prior to treatment with 14C PDC and light activated. Five concentrations of d9-THC were used (0, 5, 10, 20, 40 μM). As a significant effect was only observed with a d9-THC concentration of 40 μM, only the results obtained at this concentration are shown (see FIG. 1). After 24 hours, cells were treated with 14C PDC for 4 hours, PDT was performed using green light (20 $J/cm^2$) and plates were incubated overnight for presto blue on the following day. The PDT dose used was decreased to induce 10-15% cell kill in order to highlight any additive/synergistic effect of the combination that might otherwise be masked if a higher dose had been used.

Testing showed that a cannabinoid receptor agonist plus PDT combination treatment resulted in a synergistically effective cell kill percentage, which significantly exceeded the hypothetical cell kill percentage had the combined effect merely been additive. If the effect were merely additive, there would be no additional benefit of concurrent administration over separate administration.

FIG. 1 shows d9-THC's synergistic effect when combined with PDT. Absolute cell kill values are shown with error bars representing standard deviations between wells. The hypothetical additive effect represents the hypothetical cell kill percentage had the combined effect merely been additive. Reading from left to right in FIG. 1: the first bar is the control; the second bar is d9-THC only; the third bar is light activated 14C PDC only; the fourth bar is hypothetical cell kill percentage of d9-THC combined with 14C PDC light activated; and the fifth bar is PDT (light activated 14C PDC) combined with the tested cannabinoid. PDT alone (light activated 14C PDC) induced 10% cell kill. 40 µM of d9-THC induced 10% cell kill. If the effect of the combination were strictly additive, the combined cell kill would aggregate to 20% (hypothetical additive); however, the observed combined cell kill was 35% (light activated 14C PDC+d9-THC), demonstrating that the combination of the two treatment methodologies achieved a synergistic effect.

Figure 2:
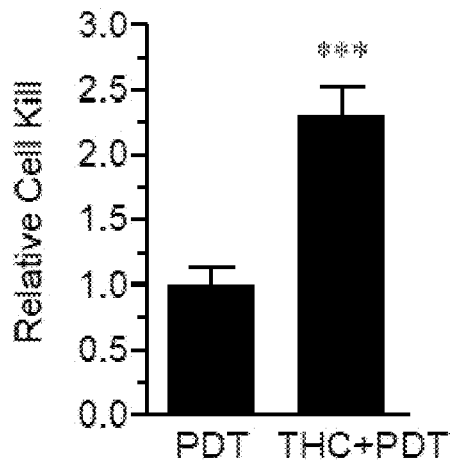
FIG. 2 is a bar graph of relative cell kill.

FIG. 2 illustrates the effect of d9-THC when combined with PDT as the relative increase in effect versus PDT effect alone.

Without wishing to be bound by theory, the observed increase in cell kill may be due to changes in cell signaling in the cells that makes them more susceptible to destruction by PDT.

Example 2—Radio-Enhancement Effects

U87 (human primary glioblastoma) cells and HeLa cells were plated on day 1 and treated for 4 hours with RUTHERRIN (3 µM of a 3:1 mixture of apo-Transferrin and TLD1433, which is a PDC having the structure shown below).

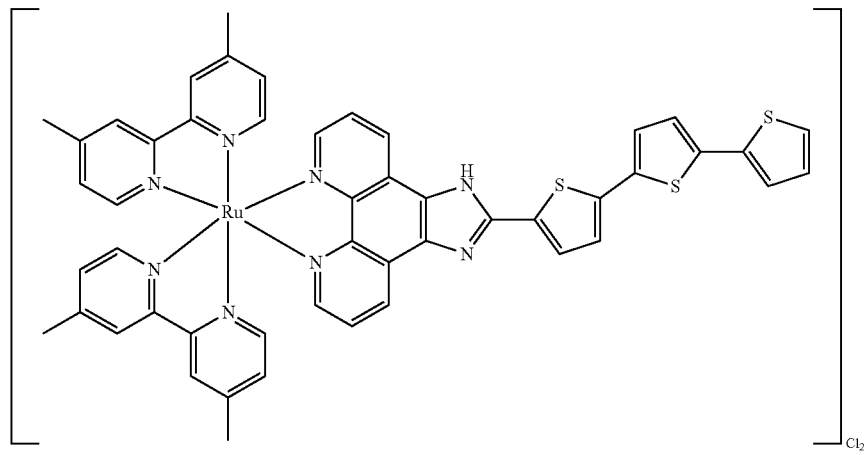

Figure 3:
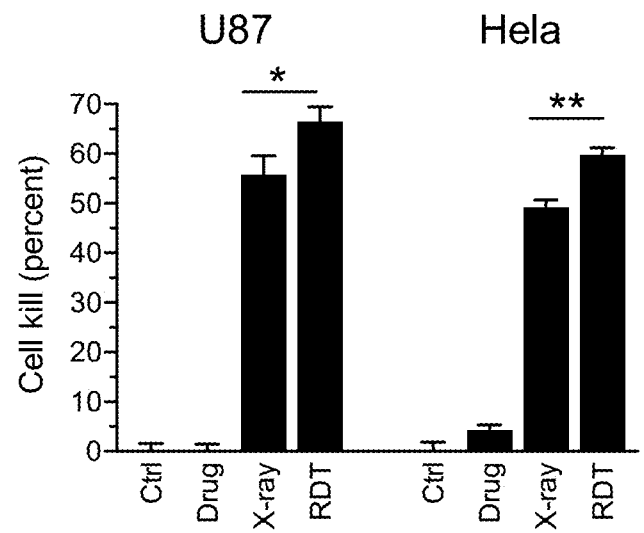
FIG. 3 is a bar graph of cell kill percentages.

The cells were then exposed to radiation (6 MeV source, 2 Gy/min). The media was then changed, and plates were incubated for 9 days to allow colony formation and assessment of cell kill. As shown in FIG. 3, the control ("Ctrl") had no effect. The drug alone ("Drug") either had no or minimal (<5%) effect. X-ray alone ("X-ray") caused about 50% cell kill and the combination ("RDT" or Radiation Dynamic Therapy) increased the cell kill to about 60% (1.2 fold increase or 10% increase in cell kill).

While the invention has been described in detail and with reference to specific examples thereof, it will be apparent to one skilled in the art that various changes and modifications can be made therein without departing from the spirit and scope thereof.

What is claimed is:

1. A method for treating cancer, said method comprising the steps of:
   (a) administering to a subject having cancer cells a composition comprising at least one cannabinoid receptor agonist;
   (b) administering to the subject a photodynamic compound; and
   (c) administering radiation to the subject in whom the at least one cannabinoid receptor agonist and the photodynamic compound are present so as to activate the photodynamic compound to generate at least one of radicals and reactive oxygen species to destroy the cancer cells to treat the cancer.

2. The method of claim 1, wherein the at least one cannabinoid receptor agonist is delta9-tetrahydrocannabinol.

3. The method of claim 1, wherein the radiation is infrared light, visible light, X-rays or other ionizing radiation.

4. The method of claim 1, wherein the at least one cannabinoid receptor agonist, the photodynamic compound and the radiation are administered in amounts synergistically effective to treat the cancer.

5. The method of claim 1, wherein the composition is administered so as to administer to the subject the at least one cannabinoid receptor agonist in an amount of at least 40 µM.

6. The method of claim 1, wherein the photodynamic compound is administered to the subject before step (a) is conducted.

7. The method of claim 6, wherein the photodynamic compound is administered in combination with a metal binding glycoprotein.

8. The method of claim 7, wherein the photodynamic compound is represented by the following structure:

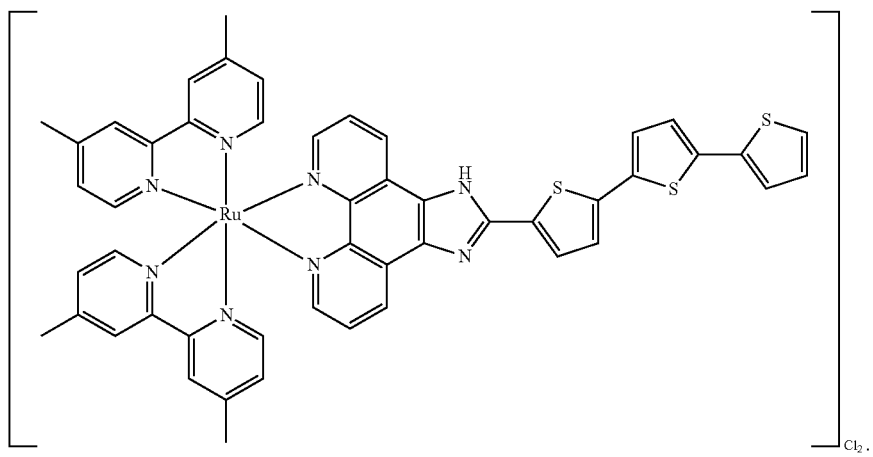

9. The method of claim 8, wherein the metal binding glycoprotein is transferrin.

10. The method of claim 9, wherein the at least one cannabinoid receptor agonist, the photodynamic compound and the radiation are administered in amounts synergistically effective to treat the cancer.

11. The method of claim 10, wherein the at least one cannabinoid receptor agonist is delta9-tetrahydrocannabinol.

12. The method of claim 11, wherein the radiation is infrared light, visible light or X-rays.

13. The method of claim 1, wherein the photodynamic compound is a metallosupramolecular complex containing at least one transition metal selected from the group consisting of osmium, manganese, molybdenum, rhenium, ruthenium, iron, cobalt, rhodium, iridium, nickel, platinum, and copper.

14. The method of claim 13, wherein the at least one cannabinoid receptor agonist is delta9-tetrahydrocannabinol.

15. The method of claim 14, wherein the radiation is infrared light, visible light or X-rays.

16. The method of claim 15, wherein the photodynamic compound is administered in combination with a metal binding glycoprotein.

17. The method of claim 1, wherein the at least one cannabinoid receptor agonist is cannabidiol.

18. The method of claim 10, wherein the at least one cannabinoid receptor agonist is cannabidiol.

19. The method of claim 18, wherein the radiation is ionizing radiation.

20. A method for treating cancer, said method comprising the steps of:
(a) administering to a subject having cancer cells a composition comprising at least one cannabinoid receptor agonist;
(b) administering to the subject a photodynamic compound represented by the following structure:

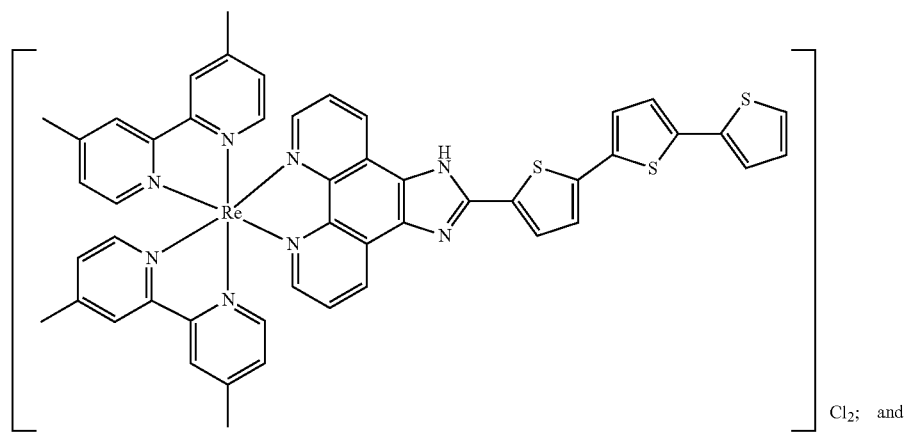

(c) administering radiation to the subject in whom the at least one cannabinoid receptor agonist and the photodynamic compound are present so as to destroy the cancer cells to treat the cancer.

* * * * *